US008846864B2

(12) United States Patent
Anderson et al.

(10) Patent No.: US 8,846,864 B2
(45) Date of Patent: Sep. 30, 2014

(54) PURIFICATION TAGS OF SYNTHETIC PEPTIDES AND PROTEINS

(75) Inventors: David William Anderson, Gladsmuir (GB); Graham John Cotton, Gladsmuir (GB); Alastair Mackie Hay, Gladsmuir (GB); Paul William Armstrong, Northern Ireland (GB); Ian Wilson, Northern Ireland (GB)

(73) Assignee: Almac Sciences (Scotland) Limited, East Lothian (GB)

( * ) Notice: Subject to any disclaimer, the term of this patent is extended or adjusted under 35 U.S.C. 154(b) by 0 days.

(21) Appl. No.: 13/634,706

(22) PCT Filed: Mar. 16, 2011

(86) PCT No.: PCT/GB2011/000363
§ 371 (c)(1),
(2), (4) Date: Sep. 13, 2012

(87) PCT Pub. No.: WO2011/114099
PCT Pub. Date: Sep. 22, 2011

(65) Prior Publication Data
US 2013/0211047 A1    Aug. 15, 2013

(30) Foreign Application Priority Data
Mar. 16, 2010   (GB) .................................. 1004372.7

(51) Int. Cl.
C07D 215/36   (2006.01)
C07K 1/13     (2006.01)
C07K 1/22     (2006.01)

(52) U.S. Cl.
CPC ............... C07D 215/36 (2013.01); C07K 1/13 (2013.01)
USPC ........................... 530/345; 530/300; 546/177

(58) Field of Classification Search
CPC .................................. C07D 215/36; C07K 1/22

USPC .................................... 530/345, 300; 540/177
See application file for complete search history.

(56) References Cited

U.S. PATENT DOCUMENTS

| 5,296,599 A * | 3/1994 | Cohen et al. | .................. 544/235 |
| 7,964,729 B2 | 6/2011 | Imperiali | |
| 2007/0010673 A1 * | 1/2007 | Hay et al. | ...................... 544/363 |

FOREIGN PATENT DOCUMENTS

WO    WO2004106363    12/2004

OTHER PUBLICATIONS

Wagner, et al: 17. Nucleotides Part Laglycone Protection by the (2-Dansylethoxy)Carbonyl (={2-{[5-(Dimethylamino)Naphthalen-I-Yl]sulfonyl}ethoxy}Carbonyl; DNSEOC) Group—A New Variation in Oligodeoxyribonucleotide Synthesis; Helvetica Chimica Acta, Verlag Helvetica Chimica Acta, Basel, CH, Jan. 1, 1997, vol. 80, pp. 200-212.

Hay, et al: "The use of a cleavable 'Tag' moiety to dramatically increase peptide purification yield", J Peptide Sci ; Sep. 1, 2010, vol. 16, Suppl. 1, p. 70.

International Search Report, PCT/GB2011/000363, dated Jun. 1, 2011, 3 pages.

International Preliminary Report on Patentability, PCT/GB2011/000363, dated Sep. 18, 2012, 9 pages.

* cited by examiner

*Primary Examiner* — Brandon Fetterolf
*Assistant Examiner* — Yih-Horng Shiao
(74) *Attorney, Agent, or Firm* — Lathrop & Gage LLP; Brian C. Trinque

(57) ABSTRACT

The present invention relates to a series of compounds useful for effecting purification, in particular for use in purification of synthetic peptides and proteins. The compounds of the invention are particularly efficient at securely anchoring peptides or proteins to a surface and allowing the peptide or protein to become uniformly orientated, thus ensuring that substantially all of the peptide or protein is available for molecular binding to a substrate.

15 Claims, No Drawings

PURIFICATION TAGS OF SYNTHETIC PEPTIDES AND PROTEINS

RELATED APPLICATIONS

This application is a 35 U.S.C. §371 filing of International Patent Application No: PCT/GB2011/000363, which was filed on Mar. 16, 2011, and which claims priority to Great Britain Patent Application No: 1004372.7, which was filed on Mar. 16, 2010. The entire contents of the aforementioned applications are hereby incorporated herein by reference.

FIELD OF THE INVENTION

The present invention relates to a series of compounds useful for effecting purification, in particular for use in purification of synthetic peptides and proteins.

BACKGROUND TO THE INVENTION

Peptides need to be in highly pure form for analytical purposes or where biologicals are to be used as medicaments. Both synthetic and recombinant peptides generally require at least some purification as part of the manufacture process before they can be used. When attempting to separate peptides in a complex mixture some are so different from the others that purification methods based on protein size, physico-chemical properties and binding affinity are able to separate them. However, the vast majority of proteins are sufficiently similar that special measures are needed to separate mixtures. One such measure involves attaching an affinity 'tag' to a protein to give the protein a binding affinity it would not ordinarily have. If the tag makes the protein unique in the mixture, the affinity can be used to separate the protein from the others.

The inherent affinity of some amino acids, such as histidine (His), to metal ions has been utilised in the purification of some peptides and proteins. One technique involves adding a poly-His (E. Hendan and J. Porath, J. Chromatography, 1985, 323, 255-264) sequence to the terminus of the peptide or protein sequence of interest, and using the affinity of the appendage for nickel ions to selectively bind the desired product to a surface. Although effective, the poly-His tag remains a permanent feature of the parent sequence, which may affect protein folding. Moreover, the extra synthetic steps to add the tag may reduce overall yield of material.

A cleavable poly-His tag has been reported (Servion et al, EP 0827966), in which a methionine residue is inserted between the parent peptide sequence and the histidine residues. Cleavage at methionine residues is achieved selectively by treatment with cyanogen bromide which is a highly toxic reagent. Furthermore, methionine residues in the protein sequence used in the oxidised form to prevent undesired cyanogen bromide cleavage must be reduced again to obtain the native sequence, increasing complexity of the synthesis.

There are few examples of chemical tags which have been used to enhance the properties of chemically synthesised peptides and proteins. Ramage et al (R. Ramage and G. Raphy, Tetrahedron Lett., 1992, 33, 385-388) used Tbfmoc as a hydrophobic analogue to Fmoc for the purification of peptides and proteins. Tbfmoc was found to be extremely hydrophobic, and has sufficient effect on the elution of peptides and proteins with the tag appended, to assist in preparative HPLC purification. However, the Tbfmoc group was found to have such a high affinity for hydrophobic surfaces that undesired binding to surfaces was often unavoidable. Furthermore, Tbfmoc has an unfavourable effect on the solubility of peptides and proteins in aqueous systems, often resulting in difficulties during purification.

Tags that covalently bind to a functionalized solid support have been used to purify both synthetic and recombinant proteins (M. Villain, J. Vizzavona, and K. Rose, Chemistry & Biology, 2001, 8, 673-679; J Vizzavona, M. Villain, and K. Rose, Tetrahedron Lett, 2002, 8693-8696). Initially, the method was applicable only to proteins with N-terminal cysteine or threonine, but the method was tailored to be suitable for all N-terminal amino acids (J Vizzavona, M. Villain, and K. Rose, Tetrahedron Lett, 2002, 8693-8696). However, obtaining the chemical tag requires a lengthy synthesis, and where removal is required the sodium periodate cleavage step can damage the peptide or protein.

Non amino acid 'chemical' affinity tags that can be reversibly attached to peptides are disclosed in EP1628998. These tags allow the peptide to be purified by passage through a column of immobilised metal ions. Synthesis of tagged amino acids by the method taught is a multistage reaction with several difficult steps and chemical stability of the tagged peptides is suboptimal.

It would be useful if there were a compound that could be used as a tag for the affinity tagging of peptides and proteins that could address these shortcomings of the art. In particular it would be useful if there were a group of easy-to-synthesise, robust tagging molecules that obtained these advantages without any detraction from the ease in which the coupling chemistry could be carried out. There also remains a need for chemical tags which can be used for purification of a peptide and which may be efficiently and easily cleaved from the peptide whilst minimising damage to the peptide itself.

It is an object of the present invention to address any and all of these aforementioned needs in the art or at the very least to provide the public with a useful alternative to those art known methods and compounds.

SUMMARY OF THE INVENTION

In a first aspect the present invention provides a compound having the molecular formula I

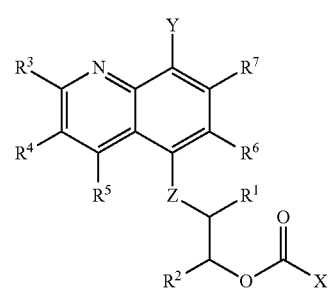

wherein:

X is a leaving group or an optionally protected amino acid derivative;

Y is OH, SH, $NH_2$, OR, SR, NHR, or NHRR' wherein R and R' are optionally substituted $C_1$-$C_6$ alkyl or acyl, or aryl, or protecting groups;

Z is S or $SO_2$;

$R^1$ and $R^2$ are each independently selected from the group hydrogen, optionally substituted alkyl, acyl or aryl and halogen; and $R^3$, $R^4$, $R^5$, $R^6$, and $R^7$ are each independently selected from the group hydrogen, optionally substituted alkyl, optionally substituted acyl, optionally substituted aryl, nitro and halogen, wherein adjacent groups may together form fused rings; and salts and derivatives thereof.

The 'leaving group' at position X may be selected from any suitable leaving groups known to the skilled chemist. In preferred embodiments the leaving group may be selected from those very commonly used in the art such as halo such as chloro, oxy-succinimidyl, or alkoxy. Any group may be used at this position which facilitates the approach and attachment of nucleophilic amino groups from the desired conjugating elements.

R and R' which are optionally attached to O, S, or N at moiety Y may be any substituted or unsubstituted $C_1$-$C_6$ alkyl, $C_1$-$C_6$ acyl, or aryl, or protecting groups such as methyl ether, methoxymethyl ether (MOM), methylthiomethyl ether (MTM), 2-methoxyethoxymethyl ether (MEM), bis(2-chloroethoxy)methyl ether, tetrahydropyranyl ether (THP), tetrahydrothiopyranyl ether, 4-methoxytetrahydrothiopyranyl ether, 4-methoxytetrahydrothiopyranyl ether, tetrahydrofuranyl ether, tetrahydrothiofuranyl ether, 1-ethoxyethyl ether, 1-methyl-1 methoxyethyl ether, 2-(phenylselenyl)ethyl ether, t-butyl ether, allyl ether, benzyl ether, o-nitrobenzyl ether, triphenylmethyl ether, α-naphthyldiphenylmethyl ether, p-methoxyphenyldiphenylmethyl ether, 9-(9-phenyl-10-oxo)anthryl ether(tritylone), trimethylsilyl ether (TMS), isopropyldimethylsilyl ether, t-butyldimethylsilyl ether (TBDMS), t-butyldiphenylsilyl ether, tribenzylsilyl ether, tribenzylsilyl ether, and triisopropylsilyl ether.

Without wishing to be bound by theory, the groups bound to the O, S or N atoms at position Y are ideally less sterically hindering, that is they are preferably either hydrogen, methyl, ethyl or propyl. Preferred compounds also have protecting groups at this position that can be removed under conditions known to the skilled person, for example those mentioned in Green, T-Protecting Groups in Organic Synthesis in particular in the reactivity charts in the appendix, to arrive at compounds according to the invention where R and R', where present, are hydrogen.

In preferred embodiments $R^1$, $R^2$, $R^3$, $R^4$, $R^5$, $R^6$, and $R^7$ are each independently hydrogen or $C_1$-$C_6$ alkyl and in more preferred embodiments one or more of $R^1$, $R^2$, $R^3$, $R^4$, $R^5$, $R^6$, and $R^7$ are hydrogen.

In some embodiments of the compound of the present invention $R^1$, $R^2$, $R^3$, $R^4$, $R^5$, $R^6$, and $R^7$ are all hydrogen but in other embodiments most of the groups are hydrogen and others, for example those at $R^4$, $R^5$, and $R^6$ are preferably lower, that is $C_1$-$C_6$, alkyl.

Without wishing to be bound by theory, the groups near the portions of the compound which during purification interact with the metal ions, that is the 'chelating' portions, are ideally less sterically hindering, that is they are preferably either hydrogen or methyl. Substitutions at this portion of the molecule in particular may hinder chelation but substitutions at other R groups is less likely to affect this interaction.

In preferred embodiments the compound of the present invention is that compound wherein Z is S.

In another preferred embodiment the compound of the present invention is that compound wherein Z is $SO_2$.

In one particularly preferred embodiment the compound of compound of the invention is that having the molecular formula II

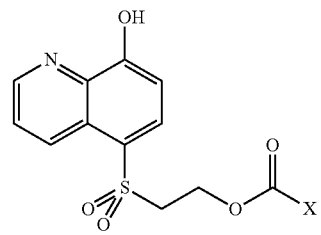

wherein X is as defined above.

Where the compound is for use in attaching to an amino terminus of a peptide then the group X is preferably a good leaving group such as N-oxo-succinimydyl and derivatives, phenoxyl and its derivatives such as, for example, paranitrophenoxy, pentafluorophenoxy, or halo, for example chloro. Any substituent at X that leads to a reasonable rate of substitution reaction is suitable for use in the compound of this particular aspect of the invention.

When the group at X is an amino acid either as part of a peptide or alone in optionally protected form, this compound may be purified by affinity chromatography. Where the X group is an optionally protected amino acid, this can be stored and used when desired in the synthesis of a peptide one desires to have an affinity tag attached to.

In a further aspect the present invention also relates to the use of the compound of the invention having Z=S as an intermediate in the production of a compound of the invention having Z=$SO_2$. During the production process one or more other groups of the molecule may also be changed under conditions used to effect oxidation from S to $SO_2$.

In another aspect of the invention there is provided a compound of formula III

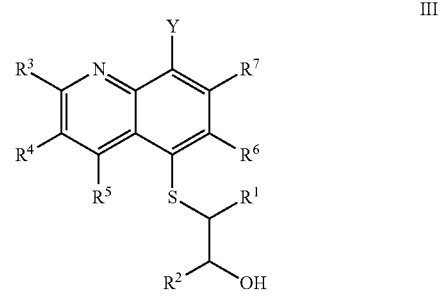

wherein $R^1$, $R^2$, $R^3$, $R^4$, $R^5$, $R^6$, $R^7$ and Y are as defined earlier. This compound is particularly preferred for use as an intermediate in the production of a compound according to the invention.

The invention also provides a method of tagging an amino acid or peptide comprising the steps of reacting the N-terminus of the amino acid or peptide, forming a carbamate bond, so as to attach a compound of the invention. The 'tagging' step allows for a further aspect of the invention; purifying an amino acid or peptide comprising tagging said amino acid or peptide in accordance with the method. Peptides tagged in this way can easily be separated from other matter in a mixture by using affinity chromatography.

In preferred embodiments the method outlined above further comprises the step of cleaving the carbamate bond under basic conditions to liberate the peptide. Preferably this step is conducted at a pH above 9, more preferably above 10 and most preferably at a pH of about 11. The higher the pH required for removal of the tag the more stable the tagged peptide is found to be.

The invention also provides an amino acid or peptide purified according to the method of the invention.

Affinity chromatography utilises a suitable 'capture receptor' which in the method section of this specification is a metal containing column. For example, the capture receptor may be provided as part of an Liquid Chromatography column.

As described above, the tag molecule of the present invention is particularly advantageous in that a peptide tagged with said molecule can easily be cleaved from the tag molecule following purification under conditions which minimise, indeed preferably prevent, damage to the peptide.

Biological assays and diagnostic tests commonly involve the binding of peptides or proteins to surfaces such as well surfaces of multi-well plates.

However, the binding of such peptides or proteins, either directly or via conventionally used tag molecules, often results in the peptides being randomly oriented on the well surface, giving results with a high background noise and poor reproducibility.

It is believed that the tag molecules of the invention are particularly efficient at securely anchoring the tag molecules to the surface and allowing the peptide or protein to become uniformly orientated, thus ensuring that substantially all of the peptide or protein is available for molecular binding to a substrate. This uniformity increases the reliability and reproducibility of a diagnostic test.

The present invention will now be discussed in detail and with reference to the following Experimental section. This is given to satisfy the 'best modes' requirement in some jurisdictions and to show how the inventive compounds may be put into use and is intended in no way to be limiting to the scope of the invention as claimed in the appended claims.

In the experimental references to Tag1 are comparative references to the compounds of EP1628998 and references to Tag2 are references to the compounds of the present invention. The preferred Tag2, that is the compound of formula II shown above where X is N-oxy-succinimydyl, is advantageously prepared according to the method in Scheme 1.

In a further embodiment, Tag2 is the compound of formula II shown above where X is paranitrophenoxy.

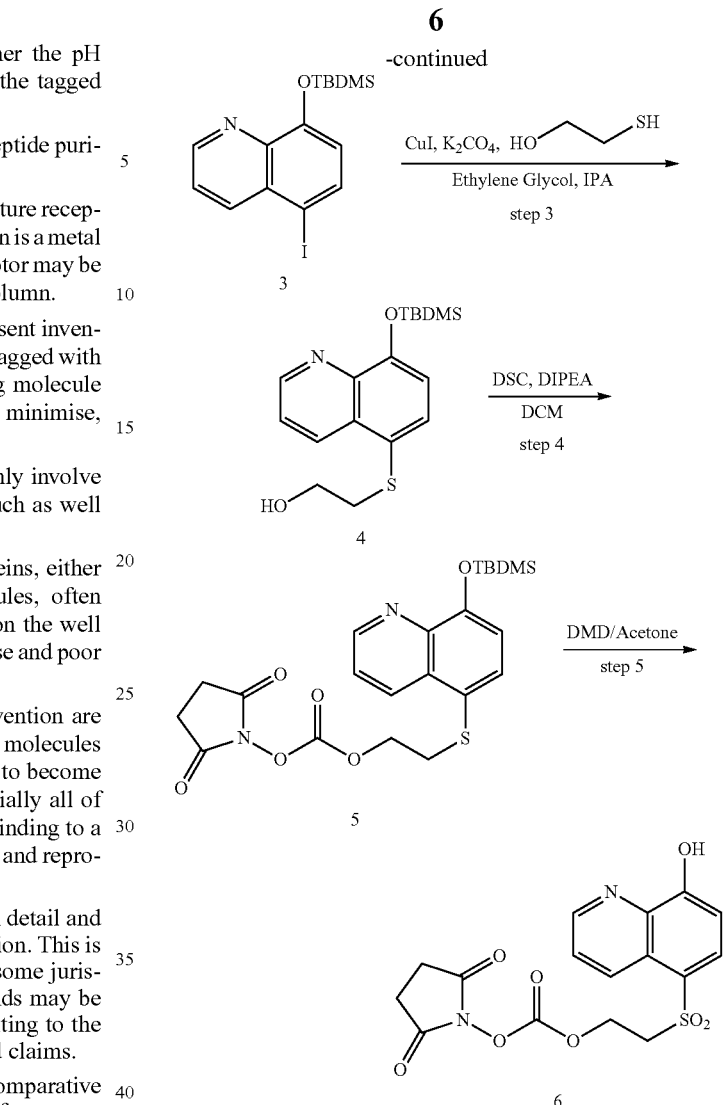

EXPERIMENTAL

Step 1:

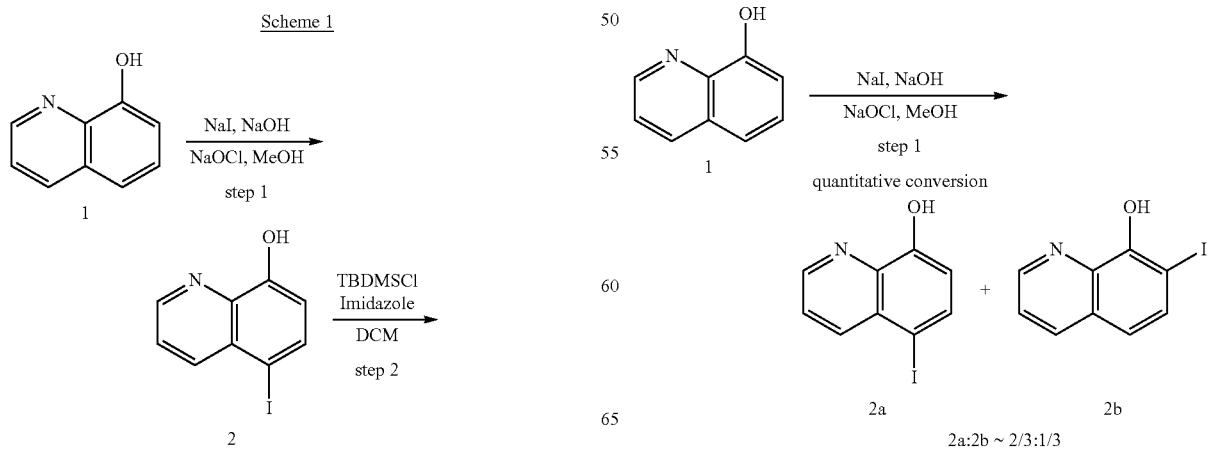

8-Hydroxyquinoline (40.00 g, 275 mmol), sodium iodide (41.33 g, 275 mmol) and sodium hydroxide (11.02 g, 275 mmol) were dissolved in methanol (1200 mL). The mixture was cooled to −40° C. and a 5% aqueous solution of NaOCl was added dropwise via an addition funnel over 30 min. The reaction mixture was vigorously stirred at −40° C. for 30 min and then quenched with a 10% aqueous solution of HCl (Check pH-6-7). The product precipitated from solution and was collected by filtration. Filtration extremely difficult, product damped. The solid was diluted in DCM and the water was azeotroped in vacuo to afford the title compound as a light yellow solid. This product was used for the next step without any further purification. m=76.60 g, yield=100%

Step 2:

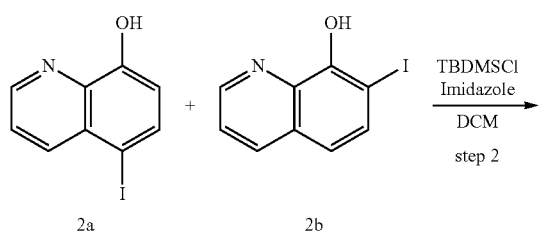

8-Hydroxy-5-iodoquinoline (22.97 g, 84.7 mmol), imidazole (12.69 g, 186.4 mmol) and tert-butyldimethyl chlorosilane (14.05 g, 93.2 mmol) were dissolved in anhydrous dichloromethane (138 mL). This reaction mixture was left to stir for 16 hours at room temperature under nitrogen. The reaction mixture was diluted with dichloromethane (100 mL), washed with 1 M HCl (100 mL) and washed with water (100 mL). The organic phase was then dried over Na$_2$SO$_4$ and concentrated in vacuo to afford a brown oil which was carefully diluted with hexane and purified by column chromatography (100% Hexane) to afford 14.18 g of a pale yellow oil which crystallise on standing. Yield 43%.

Step 3:

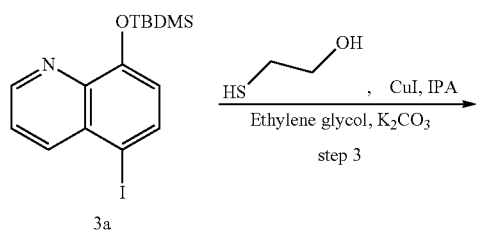

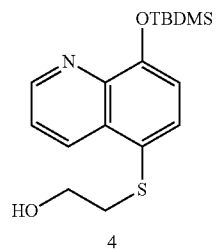

3a (2.00 g, 5.19 mmol), potassium carbonate (1.43 g, 10.38 mmol), copper iodide (0.049 g, 0.259 mmol) were charged in a 20 mL microwave vial. The vial was sealed and placed under nitrogen. Mercaptoethanol (1.091 mL, 15.57 mmol), ethylene glycol (0.579 mL, 10.38 mmol) and 2-propanol (15 mL) were added by syringe at room temperature. The vial was submitted to microwave irradiation on very high absorption at 120° C. for 1 hour. The solids were removed by filtration and the filtrate concentrated in vacuo to afford a dark yellow oil. The oil was diluted in the minimum amount of THF and purified by column chromatography (100% Hexane, 0 to 20% AcOEt then 20% AcOEt in Hexane) to afford m=1.04 g of a pale yellow oil. Yield=60%.

Step 4:

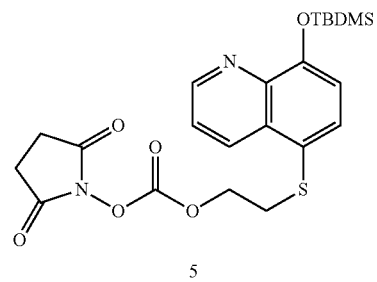

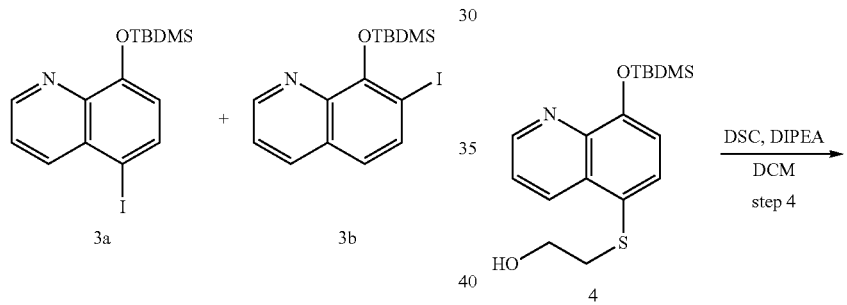

To a solution of 4 (4.51 g, 13.4 mmol) dissolved in anhydrous dichloromethane (300 mL) was added the disuccinimidyl carbonate (11.36 g, 44.3 mmol) and diisopropylethyl amine (7.02 mL, 40.3 mmol). The reaction was left to stir for 16 hours at room temperature. The reaction mixture was then quenched by addition of 5% aqueous solution of KHSO$_4$ and the organic phase was washed with water, dried over Na$_2$SO$_4$ and concentrated in vacuo to afford a pale oil. m=7.00 g, the product will be used without further purification in the next step.

Step 5:

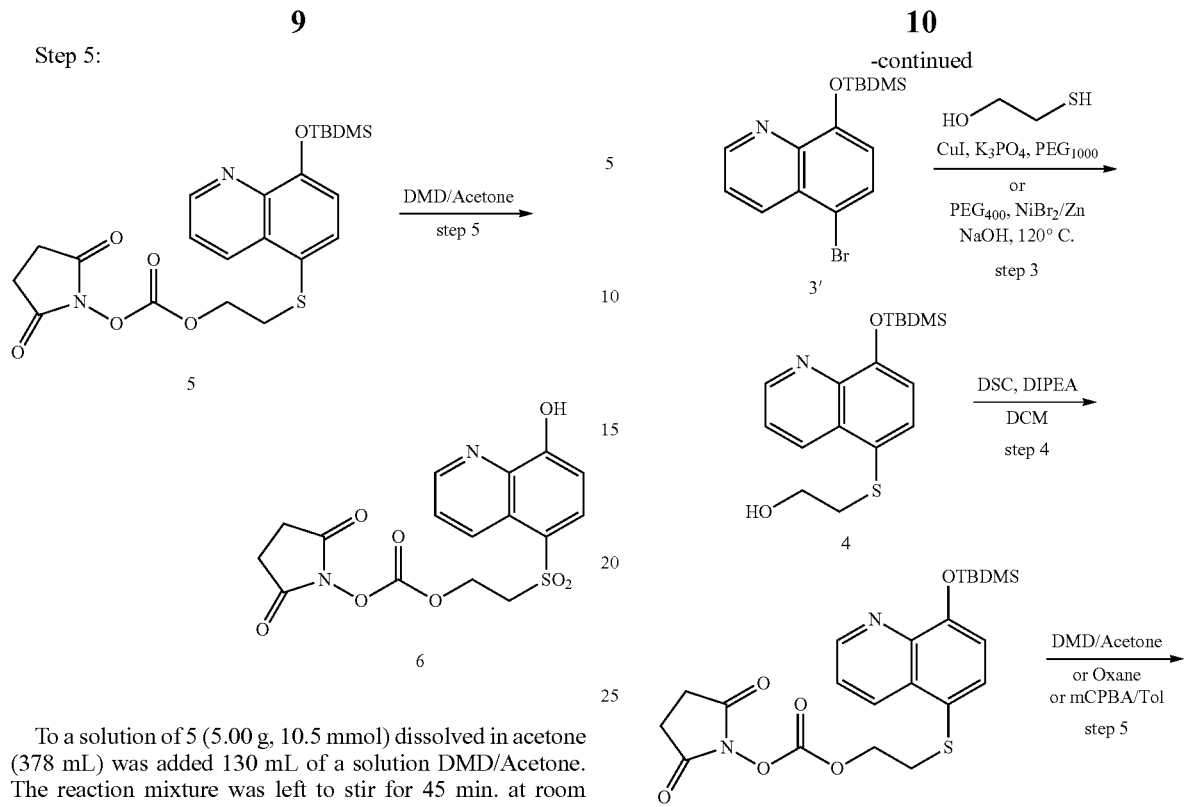

To a solution of 5 (5.00 g, 10.5 mmol) dissolved in acetone (378 mL) was added 130 mL of a solution DMD/Acetone. The reaction mixture was left to stir for 45 min. at room temperature and was monitored by LCMS. The DMD/acetone solution was again added portionwise until the LCMS show total conversion. The reaction mixture was concentrated in vacuo to afford a yellow solid which was triturated in hexane and then in THF to afford a pale yellow solid. m=2.44 g, yield=59%.

Alternative Method for the Preferred Tag 2.

Alternatively the preferred Tag2 may be prepared according to the following

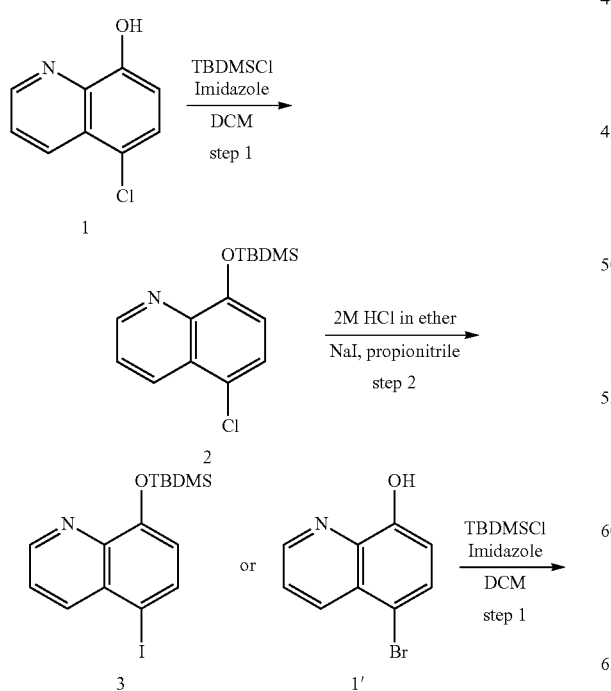

Scheme:

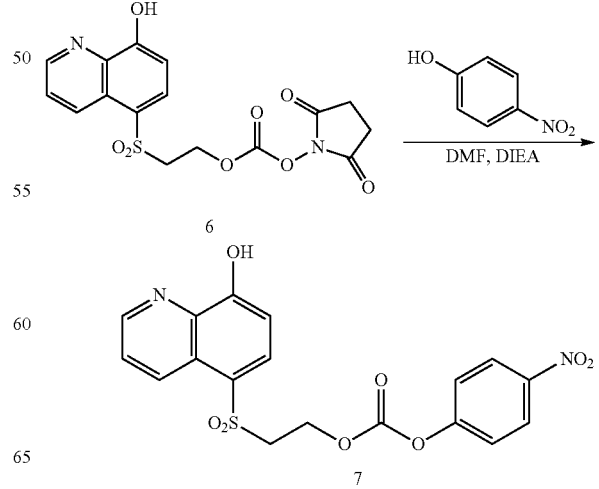

To a solution of 6 (20 mg, 0.051 mmol) in DMF (1 mL) was added p-nitrophenol (35 mg, 0.25 mmol), with diisopropylethylamine (0.025 mmol), then the solution was stirred for seventy minutes and analysed by HPLC and mass spectrometry, indicating that the desired product, 7, had formed.

Taq-Based-Purification—Experimental Details

Reagents and solvents were purchased from Aldrich, Novabiochem and Rathburn, and used as supplied unless otherwise stated. Tag reagents were prepared by Almac Sciences, Craigavon, NI, and were used as supplied.

Mass spectra were obtained on a Bruker microTOF electrospray MS. Analytical RP-HPLC was performed using an Agilent 1100 or 1200 series HPLC system with a Phenomenex Luna or Jupiter C18 column (4.6×250 mm) and a gradient of water/acetonitrile containing 0.1% TFA as specified in the text, with a flow rate of 1 ml/min. Preparative RP-HPLC was performed using a Gilson HPLC system consisting of Gilson 305 pumps, Gilson 811C dynamic mixer and an ABI 783A UV detector, with a Phenomenex Luna or Jupiter C18 column (21.2×250 mm) and a gradient of water/acetonitrile containing 0.1% TFA as specified in the text, with a flow rate of 9 ml/min. UV-vis spectra were obtained using a Varian Cary 50 Bio instrument.

IMAC chromatography was carried out using GE sepharose IMAC resins (1 ml prepacked columns containing HiTrap IMAC HP resin or HiTrap Chelating HP resin, or 2 ml manually prepared columns containing Chelating Sepharose Fast Flow resin). The metal binding ligand in the "Chelating" resins is iminodiacetic acid. The metal binding ligand in the "IMAC HP" resin is not disclosed by GE. The binding capacity of these resins was determined to be ~1 pmol tagged peptide/ml resin. IMAC runs using 1 ml columns were carried performed using a GE AKTA LC system, or manually using a syringe. IMAC runs using 2 ml columns were carried out under gravity, with the flow rate controlled by a screw clip.

IMAC buffers consisted of 20 mM sodium phosphate, 8 M urea and 0.5 M NaCl. The pH of the buffer was 6.5 for binding and 3.5 for elution. The resin was charged with metal ions with a 0.1 M solution of $CuSO_4$ or $NiCl_2$. Cleavage of the IMAC Tags was carried out by adjustment of the pH of the solution of tagged peptide to 8.5 for 30 min (for Tag1) or 11 for 1 hour (Tag2). On completion of the IMAC run, metal ions were removed from the resin by treatment with a solution of 0.5 M EDTA in the above buffer at pH 7.5.

Example IMAC Protocol for 2 ml Manual Column

1) Load with Metal Ion Solution Wash column with 10 ml pure water. Add 1 ml 0.1 M metal solution. Wash with 10 ml pure water.

2) Pre-Run Equilibration

Wash with 3×5 ml Elute buffer. Wash with 4×5 ml Bind buffer.

3) Bind and Wash

Dissolve crude tagged material [1 mg/ml] in Bind buffer. Load onto column at low flow rate (0.1-0.25 ml/min). Wash with 1 ml Bind buffer at the same flow rate. Wash with 2×3 ml Bind buffer. Check fractions by UV to confirm binding of tagged material.

4) Elute and Re-Equilibrate

Wash with 2×7 ml Elute buffer. Wash with 2×6 ml Elute buffer. Re-equilibrate with 3×5 ml Bind buffer. Check fractions by UV to determine location of eluted material. Check by HPLC if required.

5) Cleave Tag

Combine fractions containing tagged product. Adjust to pH 8.5 (Tag1) or pH 11 (Tag2) with 2 M NaOH. Allow to stand for 30 min (Tag1) or 1 hour (Tag2), then adjust pH to ~7 with 2 M HCl.

6) Pass 2

Load combined cleaved fractions at low flow rate as before. Wash with 2 ml Bind buffer at low flow rate. Wash with 5×6 ml Bind buffer. Check fractions by UV to determine location of product. Check by HPLC if required. Wash with 2×5 ml EDTA stripping solution. Wash with 2×7 ml Bind buffer, then 3×5 ml pure water.

For 1 ml columns, the volumes above were scaled down accordingly.

Peptide Synthesis

Automated solid phase peptide synthesis was carried out on a ABI 433 peptide synthesiser with 0.20-0.25 mmol of Wang or Rink amide resins as described in the text, using standard Fmoc/tBu SPPS chemistry, with 1 mmol of Fmoc-amino acid and HOCt (ethyl-1-hydroxy-1H-1,2,3-triazole-4-carboxylate)/DIC coupling reagents per coupling cycle. Unreacted amino groups were capped by treatment with a 0.5 M solution of $Ac_2O$ in DMF. Fmoc removal was carried out by treatment with a 20% v/v solution of piperidine in DMF for 20 minutes.

Tag-Xaa-Peptides: Manual coupling of Tag-amino acids was carried out by dissolving 5 eq. Tag-AA wrt resin in min. vol. DMF and activating with equimolar amounts of 0.5 M HOBt and DIC solutions in DMF for 10 minutes. The activated acid was then added to the preswelled resin and the reaction mixture was agitated by ultrasonication at room temperature for 4 hours. Coupling yield was >90% in all cases.

Tag2-Peptides: Coupling of Tag2-succinate was carried out by dissolving 5 eq. Tag2-OSu wrt resin in min. vol. DMF and adding to the preswelled resin. The mixture was agitated by ultrasonication at room temperature for 30 min, then DIPEA (2.5 eq. wrt resin) was added and sonication was continued for a further 4 hours. Coupling yield was >90% in all cases.

Peptides were cleaved from the solid phase with concomitant side-chain deprotection by treatment with 85% TFA v/v, 2.5% EDT v/v, 5% $H_2O$ v/v, 5% thioanisole v/v, 2.5% TIS v/v, 5% phenol w/v, for 4.5 hours. The resin was removed by filtration and the crude peptide was precipitated from ice-cold ether and collected by centrifugation at 4000 rpm for 5 mins. The crude peptide was then dissolved with $MeCN/H_2O$ (50:50) and lyophilised, then purified by preparative HPLC or IMAC.

Peptide 1 (Crosstide 11mer): Sequence <u>RPRTS</u> SFAEG-$NH_2$ (SEQ ID No. 1) was synthesised on Fmoc-Rink amide resin (0.60 mmol/g loading, 0.25 mmol). Underlined residues were double coupled.

Tag1-Gly-Peptide 1: Tag1-Gly was coupled to the above resin (0.1 mmol) under the standard HOBt/DIC conditions. The peptide-resin was then subjected to standard cleavage and deprotection conditions to afford the crude peptide (206 mg). 4.0 mg of crude material was purified by preparative HPLC (Luna C18 column, 5-65% MeCN over 60 minutes). Fractions containing pure Tag1-peptide were combined and lyophilised to afford 0.88 mg product (22% recovery). The purity of the product was 92% as assessed by analytical HPLC (Luna C18 column). 4.0 mg of crude material was purified using a 2 ml IDA resin IMAC column charged with $Cu^{2+}$ using steps 1-4 of the standard protocol, to afford Tag1-Gly-Peptide 1 with a recovery of 68% and purity of 94% as determined by HPLC of the collected fractions. m/z (ESI) calculated for Tag1-GRPRTSSFAE-$NH_2$ (SEQ ID No. 2): 1754.2, observed: 1754.2 $[M]^+$.

Peptide 2 (HCV 12mer): Sequence YLLPR RGPRL GV (SEQ ID No. 3) was synthesised on Wang resin preloaded with Fmoc-Val-OH (0.56 mmol/g loading, 0.25 mmol). An initial extended capping step was carried out with 0.5 M $Ac_2O$ in DMF in the presence of a catalytic amount of DMAP for 1 hour, to ensure complete acylation of the Wang linker.

Tag1-Gly-Peptide 2: Tag1-Gly was coupled to the above resin (0.05 mmol) under the standard HOBt/DIC conditions. The peptide-resin was then subjected to standard cleavage and deprotection conditions to afford the crude peptide (85 mg). 4.0 mg of crude material was purified by preparative HPLC (Luna C18 column, 10-50% MeCN over 40 minutes). Fractions containing pure Tag1-peptide were combined and lyophilised to afford 0.84 mg product (22% recovery). The purity of the product was 95% as assessed by analytical HPLC (Luna C18 column). 4.0 mg of crude material was purified using a 2 ml IDA resin IMAC column charged with $Cu^{2+}$ using the standard protocol, to afford Gly-Peptide 2 with a recovery of 85% and purity of 96% as determined by HPLC of the collected fractions. m/z (ESI) calculated for GYLLP RRGPR LGV (SEQ ID No. 4): 1452.9, observed: 1452.9 $[M]^+$.

Tag2-Val-Peptide 2: Tag2-Val was coupled to Peptide 2 resin (0.05 mmol) under the standard HOBt/DIC conditions. The peptide-resin was then subjected to standard cleavage and deprotection conditions to afford the crude peptide (86 mg). 4.2 mg of crude material was purified by preparative HPLC (Luna C18 column, 10-50% MeCN over 40 minutes). Fractions containing pure Tag1-peptide were combined and lyophilised to afford 0.88 mg product (21% recovery). The purity of the product was 95% as assessed by analytical HPLC (Luna C18 column). 4.0 mg of crude material was purified using a 2 ml IDA resin IMAC column charged with $Cu^{2+}$ using the standard protocol, to afford Val-Peptide 2 with a recovery of 89° A) and purity of 97% as determined by HPLC of the collected fractions. m/z (ESI) calculated for VYLLP RRGPR LGV (SEQ ID No. 5): 1494.9, observed: 1494.9 $[M]^+$.

Tag2-Peptide 2: Tag2-OSu was coupled to Peptide 2 resin (0.19 mmol) under the standard conditions. The peptide-resin was then subjected to standard cleavage and deprotection conditions to afford the crude peptide (298 mg). 3.1 mg of crude material was purified using a 2 ml IDA resin IMAC column charged with $Cu^{2+}$ using the standard protocol, to afford Tag1-peptide with a recovery of 95% and purity of 97% as determined by HPLC of the collected fractions. m/z (ESI) calculated for YLLP RRGPR LGV (SEQ ID No. 6): 1395, 9, observed: 1395.9 $[M]^+$.

Peptide 3a (ELC 61-98): Sequence FTTLR GRQLC APPDQ PWVER IIQRL QRTSA K(Nle)KRR SS (SEQ ID No. 7) was synthesised on Chematrix Wang resin preloaded with Fmoc-Ser(Trt)-OH (0.39 mmol/g loading, 0.19 mmol). An initial extended capping step was carried out with 0.5 M $Ac_2O$ in DMF in the presence of a catalytic amount of DMAP for 1 hour, to ensure complete acylation of the Wang linker. Underlined residues were double coupled.

Tag1-Val-Peptide 3a: Tag2-Val was coupled to Peptide 3a resin (0.05 mmol) under the standard HOBt/DIC conditions. The peptide-resin was then subjected to standard cleavage and deprotection conditions to afford the crude peptide (90 mg). 12.0 mg of crude material was purified by preparative HPLC (Jupiter C18 column, 10-70% MeCN over 60 minutes). Fractions containing pure Tag1-peptide were combined and lyophilised to afford 2.4 mg product (20% recovery). The purity of the product was 95% as assessed by analytical HPLC (Jupiter C18 column). m/z (ESI) calculated for Tag1-VFTTLRGRQLC APPDQPWVERIIQRLQRTSAK(Nle) KRRSS (SEQ ID No. 8): 5085.1, observed: 5084.9 $[M]^+$. Isolation of Peptide 3a by IMAC using IDA resin was not successful due to the formation of heterodimers during purification.

Peptide 3b (ELC 61-98): Sequence FTTLR GRQ LC(StBu) APPDQ PWVER IIQRL QRTSA K(Nle)KRR SS (SEQ ID No. 9) was synthesised on Chematrix Wang resin preloaded with Fmoc-Ser(Trt)-OH (0.39 mmol/g loading, 0.19 mmol). An initial extended capping step was carried out with 0.5 M $Ac_2O$ in DMF in the presence of a catalytic amount of DMAP for 1 hour, to ensure complete acylation of the Wang linker. Underlined residues were double coupled.

Tag2-Peptide 3b: Tag2-OSu was coupled to Peptide 3b resin (0.07 mmol) under the standard conditions. The peptide-resin was then subjected to treatment with 90% TFA v/v, 5% $H_2O$ v/v, 5% TIS v/v, for 4.5 hours. The resin was removed by filtration and the crude peptide was precipitated from ice-cold ether and collected by centrifugation at 4000 rpm for 5 mins. The crude peptide was then dissolved with $MeCN/H_2O$ (50:50) and lyophilised to afford the crude peptide (90 mg). 11.0 mg of crude material was purified using a 2 ml IDA resin IMAC column charged with $Cu^{2+}$ using the standard protocol, to afford Peptide3b. The combined fractions of pure peptide (29 ml) were treated with TCEP (41 mg, 5 mM) at pH 8-8.5 for 1 hour to afford Peptide 3a with a recovery of 52% and purity of 83% as determined by HPLC. m/z (ESI) calculated for FTTLRGRQLC APPDQPWVERI-IQRLQRTSAK(Nle)KRRSS (SEQ ID No. 10): 4394.1, observed: 4393.5 $[M]^+$.

Peptide 4 (Gly-GLP 2-36): Sequence GDEFE RHAEG TFTSD VSSYL EGQAA KEFIA WLVKG R-$NH_2$ (SEQ ID No. 11) was synthesised on Chematrix Rink amide resin (0.49 mmol/g loading, 0.20 mmol). Underlined residues were double coupled.

Tag2-Peptide 4: Tag2-OSu was coupled to Peptide 4 resin (0.05 mmol) under the standard conditions. The peptide-resin was then subjected to standard cleavage and deprotection conditions to afford the crude peptide (55 mg). 10.0 mg of crude material was purified by preparative HPLC (Jupiter C18 column, 10-70% MeCN over 60 minutes). Fractions containing pure Tag2-peptide were combined and lyophilised to afford 0.5 mg product (5% recovery). The purity of the product was 81% as assessed by analytical HPLC (Jupiter C18 column). 10.0 mg of crude material was purified using a 2 ml IDA resin IMAC column charged with $Cu^{2+}$ using the standard protocol, to afford Peptide 4 with a recovery of 22% and purity of 89% as determined by HPLC of the collected fractions. m/z (ESI) calculated for GDEFERHAEGTFTSD-VSSYLEGQAAKEFIAWLVKGR-$NH_2$ (SEQ ID No. 12): 4031.4, observed: 4031.0 $[M]^+$.

Peptide 5 (Ubiquitin): Sequence MQIFV KTLTG KTITL EVEPS DTIEN VKAKI QDKEG IPPDQ QRLIF AGKQL EDGRT LSDYN IQKES TLHLV LRLRG G (SEQ ID No. 13) was synthesised on Chematrix Wang resin preloaded with Fmoc-Gly-OH (0.32 mmol/g loading, 0:15 mmol). An initial extended capping step was carried out with 0.5 M $Ac_2O$ in DMF in the presence of a catalytic amount of DMAP for 1 hour, to ensure complete acylation of the Wang linker. Underlined residues were double coupled.

Tag1-Gly-Peptide 5: Tag1-Gly was coupled to Peptide 5 resin (0.05 mmol) under the standard HOBt/DIC conditions. The peptide-resin was then subjected to standard cleavage and deprotection conditions to afford the crude peptide (146 mg). 28.0 mg of crude material was purified by preparative HPLC (Jupiter C18 column, 10-70% MeCN over 60 minutes). Fractions containing pure Tag1-peptide were combined and lyophilised to afford 6.0 mg product (21% recovery). The purity of the product was 82% as assessed by analytical HPLC (Jupiter C18 column). 24.0 $m_g$ of crude material was purified using a 2 ml IDA resin IMAC column charged with $Cu^{2+}$ using the standard protocol, to afford Gly-Peptide 5 with a recovery of 60% and purity of 83% as determined by HPLC of the collected fractions. The isolated material contained 11% of the methionine-oxidised product. m/z (ESI) calculated for GMQIFVKTLTGKTITLEVEPSDTIEN-VKAKIQDKEGIPPDQQRLIFAGKQLEDGRT LSDY-NIQKESTLHLVLRLRGG (SEQ ID No. 14): 8621.9, observed: 8621.6 [M]$^+$.

Tag2-Peptide 5: Tag2-OSu was coupled to Peptide 5 resin (0.05 mmol) under the standard conditions. The peptide-resin was then subjected to standard cleavage and deprotection conditions to afford the crude peptide (233 mg). 13.0 mg of crude material was purified using a 2 ml IDA resin IMAC column charged with Cu$^{2+}$ using the standard protocol, to afford Peptide 5 with a recovery of 62% and purity of 89 as determined by HPLC of the collected fractions. The isolated material contained 6% of the methionine-oxidised product. m/z (ESI) calculated for MQIFVKTLTGKTI TLEVEPSD-TIENVKAKIQDKEGIPPDQQRLIF-AGKQLEDGRTLSDYNIQKESTLHLVL RLRGG (SEQ ID No. 15): 8564.9, observed: 8564.6 [M]$^+$.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments.

Indeed, various modifications of the described modes of carrying out the invention which are obvious to those skilled in the art are intended to be covered by the present invention.

The invention claimed is:

1. A compound having the molecular formula I

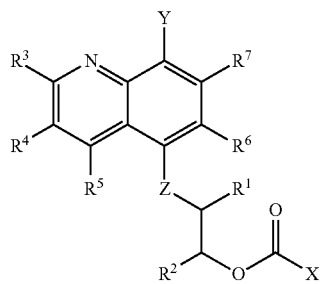

wherein:
- X is a leaving group or an optionally protected amino acid either alone or as part of a peptide;
- Y is OH, SH, $NH_2$, OR, SR, NHR, or NHRR' wherein R and R' are optionally substituted $C_1$-$C_6$ alkyl or acyl, or aryl, or protecting groups;
- Z is S or $SO_2$;
- $R^1$ and $R^2$ are each independently selected from the group consisting of hydrogen, optionally substituted alkyl, acyl, aryl and halogen; and
- $R^3$, $R^4$, $R^5$, $R^6$, and $R^7$ are each independently selected from the group consisting of hydrogen, optionally substituted alkyl, optionally substituted acyl, optionally substituted aryl, nitro and halogen, wherein adjacent groups may together form fused rings; and salts thereof.

2. The compound of claim 1 wherein $R^1$, $R^2$, $R^3$, $R^4$, $R^5$, $R^6$, and $R^7$ are each independently hydrogen or $C_1$-$C_6$ alkyl.

3. The compound of claim 1 wherein one or more of $R^1$, $R^2$, $R^3$, $R^4$, $R^5$, $R^6$, and $R^7$ are hydrogen.

4. The compound of claim 1 wherein $R^1$, $R^2$, $R^3$, $R^4$, $R^5$, $R^6$, and $R^7$ are hydrogen.

5. The compound of claim 1 wherein Z is S.

6. The compound of claim 1 wherein Z is $SO_2$.

7. The compound of claim 1, wherein the compound has molecular formula II

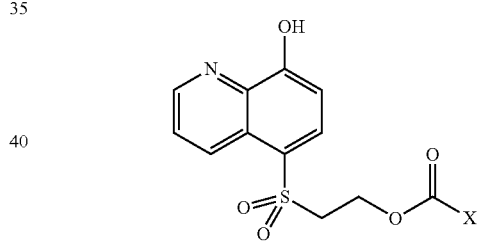

wherein X is as defined in claim 1.

8. The compound of claim 5, which is an intermediate in a production of the compound of claim 6.

9. A compound of formula III

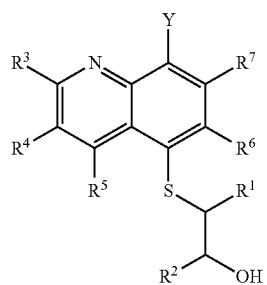

wherein $R^1$, $R^2$, $R^3$, $R^4$, $R^5$, $R^6$, $R^7$ and Y are as defined in claim 1.

10. The compound according to claim 9, wherein the compound is an intermediate in a production of the compound according to claim 1.

11. The compound according to claim 9, wherein the compound is an intermediate in a production of the compound according to claim 5 wherein that compound according to claim 5 is subsequently oxidised to give the compound according to claim 6.

12. The compound of claim 1 wherein the optionally protected amino acid at substituent X is a peptide.

13. A method of tagging an amino acid or peptide comprising the steps of introducing and incubating the compound of claim 1 to react with the N-terminus of the amino acid or peptide to form a carbamate bond.

14. A method of purifying an amino acid or peptide comprising tagging said amino acid or peptide in accordance with the method of claim 13, and separating the tagged amino acid or protein from the untagged amino acid or protein.

15. The method of claim 14 further comprising the step of cleaving the carbamate bond under basic conditions.

\* \* \* \* \*

```
                        SEQUENCE LISTING

<160> NUMBER OF SEQ ID NOS: 15

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: NH2 at 3' end

<400> SEQUENCE: 1

Arg Pro Arg Thr Ser Ser Phe Ala Glu Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Tag1 compound at 5' end
<220> FEATURE:
<221> NAME/KEY: MOD_RES
<222> LOCATION: (10)..(10)
<223> OTHER INFORMATION: NH2 at 3' end

<400> SEQUENCE: 2

Gly Arg Pro Arg Thr Ser Ser Phe Ala Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Tyr Leu Leu Pro Arg Arg Gly Pro Arg Leu Gly Val
1               5                   10

<210> SEQ ID NO 4
<211> LENGTH: 13
<212> TYPE: PRT
<213> ORGANISM: Artificial Sequence
```

```
<220> FEATURE:
<223> OTHER INFORMATION: Synthetic peptide

<400> SEQUENCE: 4

Gly Tyr Leu Leu Pro Arg Arg Gly Pro Arg Leu Gly Val
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide

<400> SEQUENCE: 5

Val Tyr Leu Leu Pro Arg Arg Gly Pro Arg Leu Gly Val
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Tyr Leu Leu Pro Arg Arg Gly Pro Arg Leu Gly Val
1               5                   10

<210> SEQ ID NO 7
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: Xaa is Nle

<400> SEQUENCE: 7

Phe Thr Thr Leu Arg Gly Arg Gln Leu Cys Ala Pro Pro Asp Gln Pro
1               5                   10                  15

Trp Val Glu Arg Ile Ile Gln Arg Leu Gln Arg Thr Ser Ala Lys Xaa
            20                  25                  30

Lys Arg Arg Ser Ser
        35

<210> SEQ ID NO 8
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Tag1 compound at 5' end
<220> FEATURE:
<221> NAME/KEY: misc_feature
<222> LOCATION: (33)..(33)
<223> OTHER INFORMATION: Xaa is Nle
```

<400> SEQUENCE: 8

Val Phe Thr Thr Leu Arg Gly Arg Gln Leu Cys Ala Pro Pro Asp Gln
1               5                   10                  15

Pro Trp Val Glu Arg Ile Ile Gln Arg Leu Gln Arg Thr Ser Ala Lys
            20                  25                  30

Xaa Lys Arg Arg Ser Ser
        35

<210> SEQ ID NO 9
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: Cys-StBu
<220> FEATURE:
<221> NAME/KEY: misc_feature
<222> LOCATION: (32)..(32)
<223> OTHER INFORMATION: Xaa is Nle

<400> SEQUENCE: 9

Phe Thr Thr Leu Arg Gly Arg Gln Leu Cys Ala Pro Pro Asp Gln Pro
1               5                   10                  15

Trp Val Glu Arg Ile Ile Gln Arg Leu Gln Arg Thr Ser Ala Lys Xaa
            20                  25                  30

Lys Arg Arg Ser Ser
        35

<210> SEQ ID NO 10
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: Xaa is Nle

<400> SEQUENCE: 10

Phe Thr Thr Leu Arg Gly Arg Gln Leu Cys Ala Pro Pro Asp Gln Pro
1               5                   10                  15

Trp Val Glu Arg Ile Ile Gln Arg Leu Gln Arg Thr Ser Ala Lys Xaa
            20                  25                  30

Lys Arg Arg Ser Ser
        35

<210> SEQ ID NO 11
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (36)..(36)
<223> OTHER INFORMATION: NH2 at 3' end

```
<400> SEQUENCE: 11

Gly Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 12
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (36)..(36)
<223> OTHER INFORMATION: NH2 at 3' end

<400> SEQUENCE: 12

Gly Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg
        35

<210> SEQ ID NO 13
<211> LENGTH: 76
<212> TYPE: PRT
<213> ORGANISM: Artificial Sequence
<220> FEATURE:
<223> OTHER INFORMATION: Synthetic peptide

<400> SEQUENCE: 13

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 14
<211> LENGTH: 77
<212> TYPE: PRT
<213> ORGANISM: Artificial Sequence
<220> FEATURE:
<223> OTHER INFORMATION: Synthetic peptide

<400> SEQUENCE: 14

Gly Met Gln Ile Phe Val Lys Thr Leu Thr Gly Lys Thr Ile Thr Leu
1               5                   10                  15

Glu Val Glu Pro Ser Asp Thr Ile Glu Asn Val Lys Ala Lys Ile Gln
            20                  25                  30

Asp Lys Glu Gly Ile Pro Pro Asp Gln Gln Arg Leu Ile Phe Ala Gly
        35                  40                  45
```

```
Lys Gln Leu Glu Asp Gly Arg Thr Leu Ser Asp Tyr Asn Ile Gln Lys
    50                  55                  60

Glu Ser Thr Leu His Leu Val Leu Arg Leu Arg Gly Gly
65                  70                  75

<210> SEQ ID NO 15
<211> LENGTH: 76
<212> TYPE: PRT
<213> ORGANISM: Artificial Sequence
<220> FEATURE:
<223> OTHER INFORMATION: Synthetic peptide

<400> SEQUENCE: 15

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```